United States Patent
Schoepgens et al.

(10) Patent No.: US 10,456,334 B2
(45) Date of Patent: *Oct. 29, 2019

(54) CREAM-TYPE HAIR COLORING AGENT

(71) Applicant: Henkel AG & Co. KGaA, Duesseldorf (DE)

(72) Inventors: Juergen Schoepgens, Schwalmtal (DE); Burkhard Mueller, Duesseldorf (DE); Veronique Munier, Saint Denis sur Loire (FR)

(73) Assignee: Henkel AG & Co. KGaA, Duesseldorf (DE)

( * ) Notice: Subject to any disclaimer, the term of this patent is extended or adjusted under 35 U.S.C. 154(b) by 57 days.

This patent is subject to a terminal disclaimer.

(21) Appl. No.: 15/826,693

(22) Filed: Nov. 30, 2017

(65) Prior Publication Data

US 2018/0168944 A1    Jun. 21, 2018

(30) Foreign Application Priority Data

Dec. 19, 2016   (DE) .................. 10 2016 225 379

(51) Int. Cl.
| | | |
|---|---|---|
| *A61Q 5/10* | (2006.01) | |
| *A61K 8/04* | (2006.01) | |
| *A61K 8/34* | (2006.01) | |
| *A61K 8/37* | (2006.01) | |
| *A61K 8/41* | (2006.01) | |
| *A61K 8/46* | (2006.01) | |
| *A61K 8/81* | (2006.01) | |

(52) U.S. Cl.
CPC ............... *A61K 8/042* (2013.01); *A61K 8/34* (2013.01); *A61K 8/342* (2013.01); *A61K 8/375* (2013.01); *A61K 8/41* (2013.01); *A61K 8/463* (2013.01); *A61K 8/8147* (2013.01); *A61K 8/8152* (2013.01); *A61Q 5/10* (2013.01); *A61K 2800/4324* (2013.01); *A61K 2800/48* (2013.01); *A61K 2800/882* (2013.01)

(58) Field of Classification Search
CPC . A61Q 5/10; A61K 8/342; A61K 8/41; A61K 8/34; A61K 8/375; A61K 8/8147; A61K 8/042; A61K 2800/88; A61K 2800/4324; A61K 2800/48
See application file for complete search history.

(56) References Cited

U.S. PATENT DOCUMENTS

| | | | |
|---|---|---|---|
| 8,790,417 B2 | 7/2014 | Schweinsberg et al. | |
| 10,143,634 B2 | 12/2018 | Witte et al. | |
| 2002/0010970 A1* | 1/2002 | Cottard .................. | A61K 8/342 8/405 |
| 2006/0277695 A1* | 12/2006 | Kleen .................... | A61K 8/416 8/405 |
| 2014/0196222 A1 | 7/2014 | Witte et al. | |
| 2016/0331673 A1 | 11/2016 | Ferritto et al. | |

FOREIGN PATENT DOCUMENTS

| | | |
|---|---|---|
| DE | 102009055125 A1 | 5/2011 |
| WO | 2013160263 A2 | 10/2013 |
| WO | WO 2013/160263 A2 * | 10/2013 |
| WO | 2016139126 A1 | 9/2016 |

OTHER PUBLICATIONS

STIC Search Report dated Mar. 21, 2019.*
National Institute of the Industrial Property of France, Preliminary Research Report and Written Opinion on the Patentability of the Invention, issued in French Patent Application FR1761958, dated Oct. 5, 2018.
United Kingdom, International Search Report and Written Opinion issued in International Application No. GB1719918.3, dated Aug. 22, 2018.

* cited by examiner

*Primary Examiner* — Eisa B Elhilo

(74) *Attorney, Agent, or Firm* — Lorenz & Kopf, LLP

(57) ABSTRACT

The subject of the present disclosure are intended to oxidative hair coloring, containing from about 60-about 83 weight-% water, oxidation dye precursor(e), alkalization resources and a specific mixture of a networked Copolymer of acrylic acid and non-ethoxy controlled Esters of acrylic acid with linear C10-C30 alkan mono alcohols, carboxylic acid, glyceryl fatty acid esters, surfactant, branched C10-C50-Alkanol and linear, saturated C8-C22 alkan-1-ol, whereby the coloring agent has an optimum viscosity for the application and the consistency of a gel-like cream with outstanding haptics.

20 Claims, No Drawings

CREAM-TYPE HAIR COLORING AGENT

CROSS-REFERENCE TO RELATED APPLICATION

This application claims priority to German Patent Application No. 10 2016 225 379.4, filed Dec. 19, 2017, which is incorporated herein by reference in its entirety.

TECHNICAL FIELD

The present disclosure relates to an oxidative hair coloring agent in cream form, a kit including this coloring agent and a hair coloring method using this coloring agent.

BACKGROUND

To achieve permanent, intense colors with corresponding fastness properties, so-called oxidative dyes are used. Said dyes usually contain oxidative dye precursors, so-called developer components and coupler components. The developer components join together or couple with one or more coupler components to form, under the influence of oxidants or atmospheric oxygen, the actual coloring agents. Indeed, the oxidative dyes are exemplified by outstanding, long-lasting color results. To achieve natural-looking colors, however, a mixture of a larger number of oxidative dye precursors (ODP) must normally be used; in many cases, partially-oxidizing dyes are also used to create the tinting effect.

Most of the oxidative dyes used for stabilizing the dye precursors during storage and to accelerate the reaction during oxidative application have an alkali pH value, which is set with alkalizing agents such as alkanolamines, ammonia or inorganic bases.

To produce the dye, the alkali coloring component is usually mixed with a hydrous hydrogen peroxide solution to form a homogeneous cream or a homogeneous gel, and then applied immediately to the hair to be dyed. This dye mixture remains on the hair for a period of 5 to 60 minutes, until the oxidative formation of the dye on the hair is complete. The dye mixture is then washed out.

The aforementioned oxidative precursors (OPC) and alkalizing agents are usually worked into the hair in a cosmetically suitable carrier, such as a cream, for example. The carrier guarantees a homogeneous distribution and an adequate dwell time of the hair coloring agent on the hair.

BRIEF SUMMARY

Agents for oxidative hair dyeing, kits-of-parts including the agents, and methods for oxidative hair dyeing using the agent are provided herein. In an embodiment, an agent for oxidative hair dyeing includes water, at least one oxidation dye precursor, at least one alkalizing agent, at least one cross-linked copolymer constructed from acrylic acid and non-ethoxylated esters of acrylic acid with linear C10-C30 mono-alcohols as monomers, at least one linear, saturated 1-alkanol with a hydroxy group and from about 8 to about 22 carbon atoms, at least one saturated or unsaturated alkane carboxylic acid with from about 14 to about 22 carbon atoms or a salt thereof, at least one glycerol fatty acid, at least one other surfactant, selected from anionic, zwitterionic, amphoteric and non-ionic surfactants and mixtures thereof, and at least one of branched alkanol with a hydroxy group and from about 10 to about 50 carbon atoms. The at least one glycerol fatty acid has Formula (I)

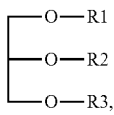

where
R1, R2 and R3 each independently of one another denote a hydrogen atom or a grouping in Formula (II),

where
R4 denotes an unbranched or branched, saturated or unsaturated $C_{11}$-$C_{27}$ alkyl group, providing that at least one and a maximum of two of the radicals, selected from R1, R2, and R3, denotes a grouping of Formula (II). Relative to the weight of the agent in each case, the agent includes the water in an amount of from about 60-about 83 wt. %, the cross-linked copolymer in a total quantity of from about 0.08-about 0.8 wt. %, the at least one linear, saturated 1-alkanol with a hydroxy group and from about 8 to about 22 carbon atoms in a total amount of from about 8-about 15 wt. %, the at least one saturated or unsaturated alkane carboxylic acid with from about 14 to about 22 carbon atoms or a salt thereof in a total amount of from about 0.1-about 2%, the at least one glycerol fatty acid in a total quantity of from about 1-about 5% wt. %, and the at least one other surfactant in a total quantity of from about 1-about 6 wt. %. The agent does not contain any oxidants.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task of the present disclosure is to provide an oxidative hair coloring agent that, by reducing the content of higher-melting, thickening fat components, exhibits a cream-like consistency, haptics and appearance with uniform or increased viscosity.

Said problems are solved by an agent for oxidative hair coloring containing the following, in each case relative to its weight:
  from about 60-about 83 wt. % water,
  at least one oxidation dye precursor,
  at least one alkalizing agent,
  at least one cross-linked copolymer, constructed from acrylic acid and non-ethoxylated esters of acrylic acid with linear C10-C30 mono-alcohols as monomers, wherein the cross-linked copolymer is contained in a total quantity of from about 0.08-about 0.8 wt. %, preferably from about 0.1-about 0.5 wt. %, particularly preferably from about 0.15-about 0.3 wt. %, in each case relative to the weight of the agent.
  at least one linear, saturated 1-alkanol with a hydroxy group and from about 8 to about 22 carbon atoms in a total amount of from about 8-about 15 wt. %, preferably from about 8.5-about 14 wt. %, particularly preferably from about 9-about 13 wt. %, at least one saturated or unsaturated alkane carboxylic acid with from about 14 to about 22 carbon atoms or a salt thereof in a total amount of from about 0.1-about 2%, preferably from about 0.2-about 1.5% wt. %, particularly preferably from about 0.3-about 0.8% wt. %, in a total quantity of from about 1-about 5% wt. %, preferably from about 1.5-about 4 wt. %, particularly preferably from about 2-about 3 wt. %, at least one glycerol fatty acid from Formula (I)

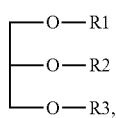
(I)

where

R1, R2 and R3 each independently of one another denote a hydrogen atom or a grouping in Formula (II),

(II)

where

R4 denotes an unbranched or branched, saturated or unsaturated $C_{11}$-$C_{27}$ alkyl group, providing that at least one and a maximum of two of the radicals, selected from R1, R2, and R3, denotes a grouping of Formula (II);

In addition to the aforementioned substances, at least one other surfactant, selected from anionic, zwitterionic, amphoteric and non-ionic surfactants and mixtures thereof, in a total quantity of from about 1-about 6 wt. %, preferably from about 1.4-about 5 wt. %, and particularly preferably from about 2-about 4.5 wt. %, which do not contain any oxidants exemplified by the fact that it contains at least one branched alkanol with a hydroxy group and from about 10 to about 50 carbon atoms, preferably in a total quantity of from about 0.5-about 5 wt. %, preferred from about 1-about 4% by weight or more preferred from about 1.5-about 3 wt. %.

The agent as contemplated herein constitutes the alkali dye component of an oxidative hair coloring agent. This is usually mixed immediately before application with a hydrous hydrogen peroxide preparation and then applied to the hair to be dyed. Until mixed with the hydrous hydrogen peroxide preparation, the agent as contemplated herein contains no oxidants.

Water Content

The agent as contemplated herein contains from about 60-about 83 wt. % water, preferably from about 65-about 80 wt. % water, particularly preferably from about 67-about 78 wt. % water, relative to its weight in each case:

Alkalizing Agent

The agent as contemplated herein contains at least one alkalizing agent. The alkalizing agent preferred as contemplated herein for setting the preferred pH value is selected from the group comprising ammonium hydroxide, basic amino acids, alkali hydroxides, alkanolamines, alkali metal meta silicates, alkali phosphates and alkali hydrogen phosphates, as well as the mixtures thereof. Lithium, sodium and potassium, particularly sodium or potassium are preferred for use as alkali metal ions.

The basic amino acids that can be used as alkalizing agents are preferably selected from the group of L-arginine, D-arginine, D,L-arginine, L-lysine, D-lysine, D,L-lysine, L-arginine, D-arginine, D,L-arginine, are more preferably used as alkalizing agents as contemplated herein.

The alkali hydroxides that can be used as alkalizing agents are preferably selected from sodium hydroxide and potassium hydroxide.

The alkanolamines usable as alkalization agents are preferably selected from primary amines with a $C_2$-$C_6$-alkyl base body having at least one hydroxyl group. More preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Most very particularly preferred alkanolamines as contemplated herein are selected from the group of 2-aminoethan-1-ol, 2-amino-2-methylpropan-1-ol and 2-amino-2-methyl-propan-1,3-diol. A most preferred alkalizing agent as contemplated herein is monoethanolamine (2-aminoethan-1-ol). To achieve the most odorless dye method possible and to optimize the color fastness properties of the dye, monoethanolamine is contained in a total quantity of from about 0.2-about 10 wt. %, preferably from about 0.5-about 8 wt. %, more preferably from about 1 to about 6 wt. % and most preferably from about 2 to about 4 wt. %—relative to the weight of the coloring agent as contemplated herein.

In addition to and/or instead of monoethanolamine, other preferred coloring agents as contemplated herein are ammonium hydroxide, i.e. ammonia in the form of its hydrous solution. Suitable hydrous ammonia solutions are from about 10 to about 35 percentage solutions (calculated in vol. %.) 100 g of hydrous ammonia solution with 25 vol. % $NH_3$ contain approx. 50 g of ammonia. Ammonia is preferably used in the form of a from about 20 to about 30 vol. % solution, most preferably in the form of a 25 vol. % solution.

In a most preferred embodiment, the coloring agent as contemplated herein contains ammonium hydroxide in a quantity of from about 0.2 to about 6 wt. %, preferably from about 0.3 to about 5 wt. %, more preferably from about 0.5 to about 3 wt. % and particularly preferably from about 1 to about 2 wt. %, relative to the weight of the coloring agent as contemplated herein.

Other alkalizing agents such as potassium hydroxide and sodium hydroxide can also be contained, preferably in a total quantity of from about 0.05 to about 1.5 wt. %, most preferably from about 0.1 to about 0.6 wt. %, in each case relative to the weight of the dye as contemplated herein.

In another most preferred embodiment, the coloring agent as contemplated herein contains at least one alkalizing agent in a total quantity of from about 0.02-about 0.4 mol/100 g, preferably from about 0.05-about 0.3 mol/100 g, in each case in mol of alkalizing agents per 100 grams of agent as contemplated herein.

Preferred agents as contemplated herein are exemplified by a pH value in the range of from about 8-about 12, preferably from about 9-about 11.5, more preferably from about 9.5-about 10.5, in each case measured at 20° C.

A further essential feature of the agents as contemplated herein is the content of at least one crosslinked copolymer, composed of acrylic acid and non-ethoxylated esters of acrylic acid with linear C10-C30-monoalcohols as monomers, wherein the crosslinked copolymer is present in a total amount of from about 0.08-about 0.8 wt. %, preferably from about 0.1-about 0.5 wt. %, particularly preferably from about 0.15-about 0.3 wt. %, relative to the weight of the agent in each case. At least one cross-linked copolymer from acrylic acid and non-ethoxylated esters of acrylic acid having linear C10-C30 mono-alcohols is preferably selected from copolymers having the INCI trade name of Acrylates/C10-30 Alkyl Acrylate Crosspolymer. Sucrose allyl ether or pentaerythrityl allyl ether is preferably contained as the cross-linking agent.

Cross-linked copolymers from acrylic acid and non-ethoxylated esters of acrylic acid having linear C10-C30 mono-alcohols, which are most preferred as contemplated herein, can be obtained by polymerizing a monomer mixture which—in each case about relative to its weight—contains from about 80 to about 99 wt. %, preferably from about 90 to about 98 wt. %, acrylic acid, at least one non-ethoxylated ester of acrylic acid having linear C10-C30 mono-alcohols in a total quantity of from about 0.9-about 19.9 wt. %, preferably from about 2-about 10 wt. %, as well as a cross-linking agent in a total quantity of from about 0.1-about 4 wt. %.

Other cross-linked copolymers from acrylic acids and non-ethoxylated esters having linear C10-C30 mono-alcohols, which are most preferred as contemplated herein, are exemplified in that their 0.5 wt. % dispersion in water at 25° C. and a pH value in the range of from about 5.8-about 6.3 has a viscosity in the range of from about 45,000 to about 65,000 mPas, measured by employing a Brookfield RVF or a Brookfield RVT viscometer at a rotational frequency of 20 rpm with Spindle #7.

The content of at least one networked copolymer, made up of acrylic acid and non-ethoxylated esters of acrylic acid with linear C10-C30-monoalcohols as monomers, is selected so that the viscosity of the agent as contemplated herein is preferably in the range of from about 17,000-about 40,000 mPas, more preferably from about 19,000-about 30,000 mPas, most preferably from about 22,000-about 27,000 mPas, each measured at 20° C. with a rotational viscometer (Haake VT 550) for a rotation frequency of 7.2 s$^{-1}$ with measurement geometry SV II.

Furthermore, the agent(s) used as contemplated herein contain at least one linear, saturated 1-alkanol with a hydroxy group and from about 8 to about 22 carbon atoms in a total amount of from about 8-about 15 wt. %, preferably from about 8.5-about 14 wt. %, particularly preferably from about 9-about 13 wt. %, relative to the weight of the agent in each case. As contemplated herein, it is preferable that at least one linear, saturated 1-alkanol with a hydroxy group and 8 to 22 carbon atoms selected from 1-decanol, 1-dodecanol (lauryl alcohol), 1-tridecanol, 1-tetradecanol (myristylalcohol), 1-hexadecanol (cetyl alcohol), 1-octadecanol (stearyl alcohol) and 1-eicosanol (arachyl alcohol), as well as mixtures thereof. A preferred alkanol mixture as contemplated herein is coconut alcohol, i.e. alkanol mixtures that are obtained by employing hydrogenation of coconut oil. Particularly preferred coconut alcohol as contemplated herein has the following chain length distribution, relative to its weight in each case: C10 and shorter: from about zero to about 3 wt. %, C12: from about 48-about 58 wt. %, C14: from about 18-about 24 wt. %, C16: from about 8-about 12 wt. %, C18: from about 11-about 15 wt. %, C20: from zero to about 1 wt. %. As contemplated herein, extraordinarily preferred C8-C22-alkan-1-ols are selected from 1-tetradecanol (myristyl alcohol), cetyl alcohol and stearyl alcohol and mixtures thereof, particularly mixtures of cetyl alcohol and stearyl alcohol.

The agent(s) as contemplated herein also contain at least one saturated or unsaturated alkane carboxylic acid with from about 14 to about 22 carbon atoms or a salt thereof in a mass of free alkane carboxylic acids in a converted total quantity of from about 0.1-about 2%, preferably from about 0.2-about 1.5% w/w, most preferably from about 0.3-about 0.8 wt. %, based on the weight of the agent. Myristic acid, palmitic acid, stearic acid, oleic, linoleic and linolenic acids, arachidic acid or mixtures of these fatty acids are particularly preferred. Palmitic acid, stearic acid, oleic acid and mixtures of these fatty acids are particularly preferred. At least one alkane carboxylic acid in the form of sodium, potassium and ammonium salts, as well as mono-, di- and trialkanol ammonium salts having from about 2 to about 4 carbon atoms in the alkanol group are particularly preferred as contemplated herein. Potassium oleate, ammonium oleate, monoethanol ammonium oleate, sodium oleate, potassium stearate, ammonium stearate, monoethanol ammonium stearate and sodium stearate, and mixtures of these compounds are particularly preferred as contemplated herein.

The agent(s) as contemplated herein also contain in a total quantity of from about 1-about 5% wt. %, preferably from about 1.5-about 4 wt. %, particularly preferred from about 2-about 3 wt. %, at least one glycerol fatty acid from Formula (I)

(I)

where

R1, R2 and R3 each independently of one another denote a hydrogen atom or a grouping in Formula (II),

(II)

where

R4 denotes an unbranched or branched, saturated or unsaturated $C_{11}$-$C_{27}$ alkyl group, providing that at least one and a maximum of two of the radicals, selected from R1, R2, and R3, denotes a grouping of Formula (II).

The R4 radical in Formula (II) denotes an unbranched or branched, saturated or unsaturated $C_{11}$-$C_{27}$ alkyl group. R4 preferably denotes an unbranched, saturated $C_{11}$-$C_{27}$-alkyl group. R4 more preferably denotes an unbranched, saturated $C_{13}$-$C_{23}$-alkyl group. R4 most preferably denotes an unbranched, saturated $C_{15}$-$C_{17}$-alkyl group.

In another particularly preferred embodiment, an agent according to this present disclosure is exemplified by the fact that as a glycerol fatty acid ester from Formula (I), it contains at least one one compound of the group of Formulas (Ia) to (Id).

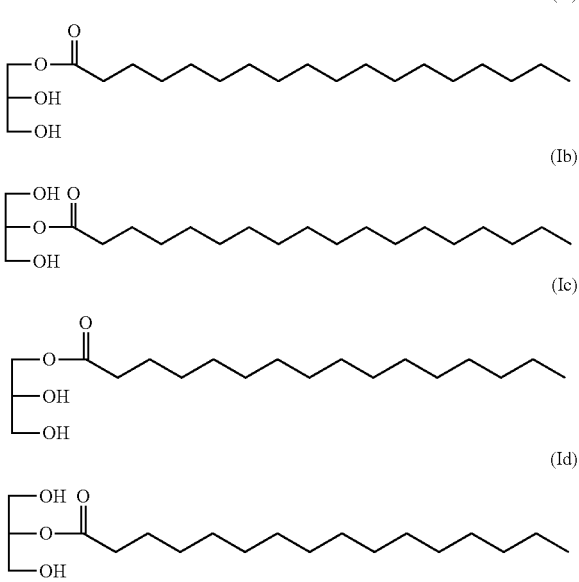

(Ia)
(Ib)
(Ic)
(Id)

The compounds of Formulas (Ia) to (Id) are also known by the names glyceryl monostearate and glyceryl monopalmitate.

In another particularly preferred embodiment, an agent according to this present disclosure is exemplified by the fact that as a glycerol fatty acid ester from Formula (I), it contains at least one one compound of the group of Formulas (Ie) to (Ih).

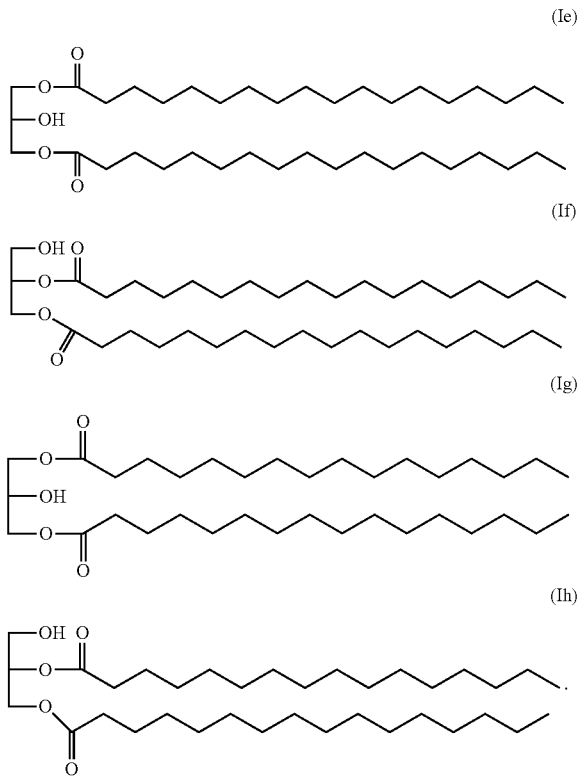 [SMILES: CCCCCCCCCCCCCCCCCC(=O)OCC(O)COC(=O)CCCCCCCCCCCCCCCCC ; CCCCCCCCCCCCCCCCCC(=O)OCC(CO)OC(=O)CCCCCCCCCCCCCCCCC ; CCCCCCCCCCCCCCCC(=O)OCC(O)COC(=O)CCCCCCCCCCCCCCC ; CCCCCCCCCCCCCCCC(=O)OCC(CO)OC(=O)CCCCCCCCCCCCCCC]

(Ie)
(If)
(Ig)
(Ih)

The compounds of Formulas (Ia) to (Id) are also known by the names glyceryl distearate and glyceryl dipalmitate.

In a very particularly preferred embodiment, agents according to this present disclosure are exemplified by the fact that as a glycerol fatty acid ester from Formula (I), it contains at least one compound selected from Formulas (Ia) to (Ih). In another very particularly preferred embodiment, an agent according to this present disclosure is exemplified by the fact that as a glycerol fatty acid from Formula (I), it contains at least one compound selected from glyceryl monostearate, glyceryl distearate, glyceryl monopalmitate and glyceryl dipalmitate.

Additional Anionic, Zwitterionic, Amphoteric or Non-Ionic Surfactants

In addition to the abovementioned linear, saturated 1-alkanols with a hydroxy group, alkane carboxylic acids with from about 14 to about 22 carbon atoms and glycerol fatty acids from Formula (I), the agent(s) used as contemplated herein contain at least one other surfactant, selected from anionic, zwitterionic, amphoteric and non-ionic surfactants and mixtures thereof, in a total quantity of from about 1-about 6 wt. %, preferably from about 1.4-about 5 wt. %, and most preferably from about 2-about 4.5 wt. %, relative to the weight of the agent in each case.

Surfactants and emulsifiers according to the present disclosure are amphiphilic (bi-functional) compounds, which includes at least one hydrophobic and at least one hydrophilic molecular part.

According to the present disclosure, saturated and unsaturated alkan-1-ols having at least 4 carbon atoms in the alk(en)yl radical, alkane carboxylic acids having at least 4 carbon atoms in the alk(en)yl radical and glycerol fatty acid mono and diesters having at least 4 carbon atoms in the fatty acid radical are not considered surfactants.

The hydrophobic radical is preferably a hydrocarbon chain with from about 8-about 30 carbon atoms, which can be saturated or unsaturated, linear or branched. It is especially preferable if this $C_8$-$C_{30}$ alkyl chain is linear. Basic properties of the surfactants and emulsifiers are oriented adsorption at boundary surfaces, as well as aggregation to micelles and the formation of lyotrophic phases.

When selecting suitable surfactants according to the present disclosure, it may be preferable to use a mixture of surfactants in order to set the properties of the oxidant dye as contemplated herein in an optimal manner.

Anionic surfactants suitable for the agents as contemplated herein are all anionic surfactants, suitable for use on the human body, which have an ionic group that renders them water-soluble, for example a sulphate, sulphonate or phosphate group, and a lipophilic alkyl group with approx. 8 to 30 C-atoms, preferably from about 8 to about 24 C-atoms in the molecule, the exception being linear and branched fatty acids with from about 8 to about 30 C-atoms and the salts thereof (soaps). Furthermore, the molecule can contain glycol or polyglycol ether groups, ester, ether and amide groups, as well as hydroxyl groups. Examples of suitable anionic surfactants, each in the form of the sodium, potassium and ammonium, as well as the mono-, di- and trialkanolammonium salts having 2 to 4 C-atoms in the alkanol group, polyethoxylated ether carboxylic acids, acylsarcosides, acyltaurides, acylisethionates, sulfosuccinic acid mono- and dialkyl esters and sulfosuccinic acid monoalkylpolyoxyethylester having from 1 to about 6 ethylene oxide groups, linear alkansulfonates, linear alpha-olefinsulfonates, sulfonates of unsaturated fatty acids having up to 6 double bonds, alpha-sulfo fatty acid methylesters of fatty acids, $C_8$-$C_{20}$ alkylsulfates and $C_8$-$C_{20}$ alkylether sulfates having from 1 to about 15 oxyethyl groups, mixed surfactant hydroxysulfonates, sulfated hydroxyalkylpolyethylene and/ or hydroxyalkylenpropylene glycol ethers, esters of tartaric acid or citric with ethoxylated or propoxylated fat alcohols, where necessary polyethoxylated alkyl- and/or alkenyletherphosphates, sulfated fatty acid alkylenglycol esters, as well as monoglyceridsulfates and monoglyceridethersulfates. Preferred anionic surfactants are selected from $C_8$-$C_{20}$ alkylsulfates, $C_8$-$C_{20}$alkylethersulfates and $C_8$-$C_{20}$ ether carboxylic acids, each having from about 8 to about 20 C-atoms in the alkyl group and from 0 to about 12 ethylenoxide groups in the molecule. Sodium laureth(2)sulfate and Sodium cetearyl sulfate, as well as mixtures thereof, are particularly preferred.

Zwitterionic surfactants are surfactant compounds, which carry a lipophilic alkyl group having approximately 8 to 30 C-atoms, preferably from about 8 to about 24 C-atoms and at least one quaternary ammonium group and at least one carboxylate, sulfonate or sulfate group. Particularly suitable zwitterionic surfactants are the so-called betaines, such as the n-alkyl-n, n-dimethylammonium glycinates, for example coco-alkyldimethyl ammonium glycinate, n-acylaminopropyl-n, n-dimethyl ammonium glycinates, for example coco-acylaminopropyldimethyl ammonium glycinate (having the INCI trade name of Cocamidopropyl Betaine), and 2-alkyl-3-carboxymethyl-3-hydroxyethyl imidazolines, each having from about 8 to about 18 carbon atoms in the alkyl or acyl group, as well as coco-acylaminoethylhydroxyethyl carboxymethyl glycinate. A preferred zwitterionic surfactant is the coco-acylaminopropyl-dimethyl ammoniumglycinate known under the INCI trade name of Cocamidopropyl Betaine.

Amphoteric surfactants are those surfactant compounds containing a $C_8$-$C_{30}$ alkyl or acyl group and at least one free amino group and at least one COOH or —$SO_3H$ group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 30 carbon atoms in the alkyl group. Particularly preferred amphoteric surfactants are N-cocosalkylaminopropionate, cocosacylaminoethylaminopropionate and $C_{12}$-$C_{18}$ acylsarcosin.

Preferred anionic or zwitterionic surfactants as contemplated herein are selected from $C_8$-$C_{20}$ alkyl sulfates, $C_8$-$C_{20}$ alkylether sulfates and $C_8$-C20ether carboxylic acids, each having from about 8 to about 20 C-atoms in the alkyl group and from 0 to about 12 ethylenoxide groups in the molecule, sodium laureth(2)sulfate being more preferred, also from coco-acylaminopropyl-dimethylammoniumglycinate and from mixtures of said surfactants.

Exceptionally preferred agents as contemplated herein contain at least one anionic or zwitterionic surfactant, selected from $C_8$-$C_{20}$ alkyl sulfates, $C_8$-$C_{20}$-alkyl ether sulfates and $C_8$-$C_{20}$ ether carboxylic acids, each with from about 8 to about 20 C-atoms in the alkyl group and from 0 to about 12 ethylene oxide groups in the molecule, wherein mixtures of sodium laureth(2)sulphate and sodium cetearyl sulfate are particularly preferred, in a total quantity of from about 0.1-about 3 wt. %, preferably from about 0.5-about 2.5 wt. %, and most preferably from about 1-about 2.1 wt. % relative to the weight of the agent in each case.

Non-ionic surfactants suitable for the agent as contemplated herein are all non-ionic surfactants suitable for use on the human body, which have at least one non-ionic group that renders them water-soluble, in particular a polyethylene glycol ether group having at least 2 ethylene oxide units, a glycoside group, in particular, a glucose or methyl glucose group, a poly glycoside group with an average of more than one glycoside unit, one polyglycerine group having at least two glycerine units, one sorbitan group, one amid group or several different of the said groups, for example, a sorbitan group and a polyethylene glycol ether group, and one lipophilic alkyl group having approximately 8 to 30 C-atoms, preferably from about 10 to about 24 C-atoms. The non-ionic surfactants most preferably used are selected from, having from about 7-about 80 mol of ethylene oxide per mol, ethoxylated castor oil, ethoxylated $C_8$-$C_{30}$ alkanols having from about 4-about 100 mol ethylene oxide per mol, ethoxylated $C_8$-$C_{24}$carbonic acid having from about 5-about 30 mol of ethylene oxide per mol, having from about 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono and oligoglycosides having from about 8 to about 22 carbon atoms in the alkyl radical and the ethoxylated analogs thereof, as well as mixtures of the aforementioned substances.

The ethoxylated $C_8$-$C_{30}$alkanols have the formula $R^1O(CH_2CH_2O)_nH$, wherein $R^1$ denotes a linear or branched alkyl and/or alkenyl radical having from about 8-about 30 carbon atoms and n, the average number of ethylene oxide units per molecule, for integers from about 4-about 100, preferably from about 6-about 30, more preferably from about 12 to about 20 mol ethylene oxide to 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from about 10-about 100 mol ethylene oxide on technical fat alcohols having from about 12-about 18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Ceteth-10, Ceteth-12, Ceteth-15, Ceteth-20, Ceteth-30, Steareth-10, Steareth-12, Steareth-15, Steareth-20 and Steareth-30, as well as the mixtures thereof, are most preferred.

The ethoxylated $C_8$-$C_{30}$carbonic acids have the formula $R^1O(CH_2CH_2O)_nH$, wherein $R^1O$ denotes a linear or branched, saturated or unsaturated acyl radical having from about 8-about 30 carbon atoms and n, the average number of ethylene oxide units per molecule, for integers from about 5-about 30, preferably from about 6-about 20, more preferably from about 6 to about 12 mol ethylene oxide to 1 mol $C_8$-$C_{30}$ carbonic acid, which is preferably selected from capryl alcohol, 2-ethylhexyl alcohol, caprin alcohol, lauric acid, isotridecaric acid, myristiric acid, cetyl acid, palmitoleic acid, stearic acid, isostearic acid, oleic acid, elaidic acid, petroselic acid, arachine acid, gadoleic acid, behenic acid, erucic acid and brassidic acid, as well as the technical mixtures thereof. Adducts from about 5-about 30, preferably from about 6-about 20, more preferably from about 6 to about 12 mol of ethylene oxide on technical fatty acids having from about 12-about 18 carbon atoms, such as coco, palm, palm kernel or sebum fat alcohols are also suitable.

As contemplated herein, particularly preferred agents contain at least one non-ionic surfactant in a total amount of from about 0.1-about 4 wt. %, preferred from about 0.3-about 3 wt. %, and most preferably from about 1-about 2.5 wt. %, calculated based on the weight of the agent.

Extraordinarily preferred agents as contemplated herein contain at least one non-ionic surfactant selected from about 7-about 80 mol ethylene oxide per mol of ethoxylated castor oil, ethoxylated $C_8$-$C_{30}$-alkanols having from about 4-about 100 mol ethylene oxide per mol, ethoxylated $C_8$-$C_{30}$-carboxylic acid having from about 5-about 30 mol of ethylene oxide per mol, with from about 4-about 50 mol of ethylene oxide per mol of ethoxylated sorbitan monoesters of linear saturated and unsaturated $C_{12}$-$C_{30}$ carbonic acids, which can be hydroxylated, and alkylmono and -oligoglycosides having from about 8 to about 22 carbon atoms in the alkyl radical and compounds of the above substances, in a total amount of from about 0.1-about 4 wt. %, more preferably from about 0.3-about 3 wt. %, and most preferably from about 1-about 2.5 wt. %, calculated based on the weight of the agent.

As contemplated herein, extraordinarily preferred agents contain a mix of sodium laureth(2)sulphate and sodium cetearyl sulfate and at least one non-ionic surfactant selected from about 7-about 80 mol ethylene oxide per mol of ethoxylated castor oil, ethoxylated $C_8$-$C_{30}$-alkanols having from about 4-about 100 mol ethylene oxide per mol, ethoxylated $C_8$-$C_{30}$-carbonic acid having from about 5-about 30 mol of ethylene oxide per mol, with from about 4-about 50 mol of ethylene oxide per mol of ethoxylated sorbitan monoesters of linear saturated and unsaturated $C_{12}$-$C_{30}$ carbonic acids, which can be hydroxylated, and alkylmono and oligoglycosides having from about 8 to about 22 carbon atoms in the alkyl radical in a total amount of from about 1-about 6 wt. %, more preferably from about 1.4-about 5 wt. %, and most preferably from about 2-about 4.5 wt. %, calculated based on the weight of the agent.

Furthermore, the agents as contemplated herein and agents used as contemplated herein contain at least one branched alkanol with a hydroxy group and from about 10 to about 50 carbon atoms. In the context of the present disclosure, at least one branched alcohol with a hydroxy group and from about 10 to about 50 carbon atoms selected from 2-hexyldecanol, 2-ocyltdodecanol, 2-ethylhexylalcohol and isostearylalcohol, as well as mixtures thereof is preferable. As contemplated herein, 2-octyldodecanol is particularly preferable. Particularly preferred agent(s) used as contemplated herein are exemplified in that they contain at least one branched alkanol having a hydroxyl group and from about 10 to about 50 carbon atoms, in a total quantity of from about 0.5-about 5 wt. %, preferably from about 1-about 4 wt. %, more preferably from about 1.5-about 3 wt. %, in each case relative to the weight of the agent. As contemplated herein, extraordinarily preferred agents as contemplated herein and extraordinarily preferred agents used as contemplated herein are exemplified in that they contain from about 0.5-about 5 wt. %, preferably from about 1-about 4 wt. %, more preferably from about 1.5-about 3 wt. %, 2-octyldodecanol, relative to the weight of the agent in each case.

The combination of the crosslinked copolymer of acrylic acid and non-ethoxylated esters of acrylic acid with linear C10-C30-monoalcohols, linear saturated 1-alkanol, alkane carboxylic acid, glycerol fatty acids and branched C10-C50-alkanol results in an especially rich, creamy consistency and haptics of the preferred color cream as contemplated herein and preferred as contemplated herein.

It may be preferred as contemplated herein that the agents as contemplated herein contain sodium polyacrylate. As contemplated herein, sodium polyacrylate preferably comprises polymers with the CAS number 9003-04-7. Sodium polyacrylates preferred as contemplated herein have an average molecular weight $M_w$ in the range from about 1,000,000 to about 20,000,000 Dalton, preferably from about 6,000,000 to about 15,000,000 Dalton. The average molecular weight $M_w$ can, for example, be determined by employing gel permeation chromatography (GPC) with polystyrene as an internal standard according to DIN 55672-3, Version 8/2007.

The preferred mixture as contemplated herein of sodium polyacrylate, crosslinked copolymers of acrylic acid and non-ethoxylated esters of acrylic acid with linear C10-C30-monoalcohols, branched C10-C50-alkanol and linear, saturated C8-C22-alkan-1-ol achieves a thickening of the agent with the optimal viscosity for the application, whereby the agent also has the consistency of a gel-like cream with outstanding haptics.

Extraordinarily preferred agents as contemplated herein contain sodium polyacrylate in a total amount of from about 0.1-about 1.5 wt. %, preferably from about 0.5-about 1.3 wt. %, particularly from about 0.8-about 1.1 wt. %, relative to the weight of the agent in each case.

In an especially preferred embodiment, the sodium polyacrylate is contained as a sodium polyacrylate pre-gelatinized in a water-in-oil emulsion. The sodium polyacrylate-containing water-in-oil emulsion preferably contains, in each case relative to its weight, from about 40-about 60 wt. % of sodium polyacrylate, from about 25-about 45 wt. % oil(s) in total, from about 0.5-about 4.9 wt. % surfactant(s) in total and from about 0.5-about 4.9 wt. % water.

The oil contained in the sodium polyacrylate-containing water-in-oil emulsion is most preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from about 2-about 30 carbon atoms with linear or branched saturated or unsaturated fatty acids having from about 2-about 30 carbon atoms, which can be hydroxylated; the adducts of from 1 to about 5 propylenoxide units of monovalent or multivalent $C_{8-22}$alkanols; the C8-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkandiols or $C_{3-22}$ alkantriols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. The oil most preferred as contemplated herein is mineral oil.

Particularly preferred is at least one surfactant selected from non-ionic surfactants contained in the sodium polyacrylate-containing water-in-oil emulsion. The non-ionic surfactants most preferably used are selected from, having from about 7-about 80 mol of ethylene oxide per mol, ethoxylated castor oil, ethoxylated $C_8$-$C_{24}$ alkanols having from about 5-about 30 mol ethylene oxide per mol, ethoxylated $C_8$-$C_{24}$carbonic acid having from about 5-about 30 mol of ethylene oxide per mol, having from about 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono and oligoglycosides having from about 8 to about 22 carbon atoms in the alkyl radical and the ethoxylated analogs thereof, as well as mixtures of the aforementioned substances.

The ethoxylated $C_8$-$C_{24}$ alkanols have the formula $R^1O(CH_2CH_2O)_nH$, wherein $R^1$ denotes a linear or branched alkyl and/or alkenyl radical having from about 8-about 24 carbon atoms and n, the average number of ethylene oxide units per molecule, for integers from about 5-about 30, preferably from about 6-about 20, more preferably from about 6 to about 12 mol ethylene oxide to 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from about 10-about 100 mol ethylene oxide on technical fat alcohols having from about 12-about 18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Trideceth-6 and Isotrideceth-6, as well as the mixtures thereof, are most preferred.

The ethoxylated $C_8$-$C_{24}$ carbonic acids have the formula $R^1O(CH_2CH_2O)_nH$, wherein $R^1O$ denotes a linear or branched, saturated or unsaturated acyl radical having from about 8-about 24 carbon atoms and n, the average number of ethylene oxide units per molecule, for integers from about 5-about 30, preferably from about 6-about 20, more preferably from about 6 to about 12 mol ethylene oxide to 1 mol $C_8$-$C_{24}$ carbonic acid, which is preferably selected from capryl alcohol, 2-ethylhexyl alcohol, caprin alcohol, lauric acid, isotridecaric acid, myristiric acid, cetyl acid, palmitoleic acid, stearic acid, isostearic acid, oleic acid, elaidic acid, petroselic acid, arachine acid, gadoleic acid, behenic acid, erucic acid and brassidic acid, as well as the technical mixtures thereof. Adducts from about 5-about 30, preferably from about 6-about 20, more preferably 6 to 12 mol of ethylene oxide on technical fatty acids having from about 12-about 18 carbon atoms, such as coco, palm, palm kernel or sebum fat alcohols are also suitable.

Agents most preferred as contemplated herein are exemplified in that they contain at least one sodium polyacrylate having an average molecular weight $M_w$ in the range from about 1,000,000 to about 20,000,000 Dalton, preferably from about 6,000,000 to about 15,000,000 Dalton, in a total quantity of from about 0.1-about 1.5 wt. %, preferably from about 0.5-about 1.3 wt. %, more preferably from about 0.8-about 1.1 wt. %, in each case relative to the total weight of the agent, wherein the sodium polyacrylate is contained pregelled in a water-in-oil emulsion, wherein said water-in-oil emulsion, in each case relative to its weight, contains from about 40-about 60 wt. % sodium polyacrylate, from about 25 about 45 wt. % oil(s) in total, preferably mineral oil, from about 0.5-about 4.9 wt. % surfactant(s) in total, preferably from about 0.5-about 4.9 wt. % non-ionic surfactant(s), and from about 0.5-about 4.9 wt. % water.

As contemplated herein, preferred and preferably used agents contain, in addition to the at least one branched alkanol having a hydroxyl group and from about 10 to about 50 carbon atoms, at least one additional oil in a total amount of from about 0.2-about 6 wt. %, preferably from about 0.5-about 5 wt. %, particularly from about 0.7-about 3 wt. %, relative to the weight of said agent in each case, wherein these quantities include the oils from the optionally contained preferred sodium polyacrylate emulsion as contemplated herein. This additional oil can be selected from the same oils that can also be comprised in the sodium polyacrylate emulsions preferred as contemplated herein. It is preferable that the at least one additional is selected from natural and synthetic hydrocarbons, particularly preferably from mineral oil, paraffin oils, $C_{18}$-$C_{30}$-isoparaffins, particularly isoeicosane, polyisobutenes and polydecenes, $C_8$-$C_{16}$ isoparaffins, and 1,3-di (2-ethylhexyl)-cyclohexane; the benzoic esters of linear or branched $C_{8-22}$-alkanols; triglycerides of linear or branched, saturated or unsaturated, optionally hydroxylated $C_{8-30}$-fatty acids, in particular natural oils; the dicarboxylic acid esters of linear or branched $C_2$-$C_{10}$-alkanols; the esters of the linear or branched saturated or unsaturated fatty alcohols having from about 2 to about 30 carbon atoms, branched saturated or unsaturated fatty acids having from about 2 to about 30 carbon atoms, which can be hydroxylated; the addition products of from 1 to about 5 propylene oxide units to mono- or polyhydric $C_{8-22}$-alkanols; the $C_8$-$C_{22}$-fatty alcohol esters of monohydric or polyhydric $C_2$-$C_7$-hydroxycarboxylic acids; the symmetrical, asymmetric or cyclic esters of carbonic acid with $C_{3-22}$-alkanols, $C_{3-22}$-alkane diols or $C_{3-22}$-alkane triols; the esters of dimeric unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances. As contemplated herein particular preference is given to oils selected from paraffin oils, natural oils, in particular amaranth seed oil, apricot kernel oil, argan oil, avocado oil, babassu oil, cottonseed oil, borage seed oil, cameline oil, safflower oil, peanut oil, pomegranate core oil, grapefruit seed oil, hemp oil, hazelnut oil, palm seed oil, jojoba oil, linseed oil, macadamia nut oil, corn oil, almond oil, manila oil, evening primrose oil, olive oil, palm oil, palm kernel oil, parannut oil, pecknut oil, peach kernel oil, rapeseed oil, castor oil, sandalwood oil, castor oil, sesame oil, soya oil, sunflower oil, grapeseed oil, walnut oil, wild-type oil, wheat germ oil, and the liquid fractions of coconut oil, and also synthetic triglyceride oils, in particular capric/caprylic triglycerides, furthermore the esters of linear or branched saturated or unsaturated fatty alcohols having from about 2-about 30 carbon atoms with linear or branched saturated or unsaturated fatty acids having from about 2-about 30 carbon atoms, which can be hydroxylated, in particular isopropyl palmitate and isopropyl myristate, and mixtures of the aforementioned oils.

A further essential feature of the agent as contemplated herein is the content of at least one oxidation dye precursor.

On the basis of their reaction behavior, oxidative dye precursors can be divided into two categories, so-called developer components and coupler components.

During the oxidative dyeing process, coupler components do not achieve any significant coloration by themselves. They always require the presence of developer components. Developer components can combine together to form the actual dye.

The developer and coupler components are normally used in a free form. In the case of substances with amino groups, however, use of the salt form thereof, more particularly in the form of hydrochlorides and hydrobromides or sulfates, may be preferred.

Oxidation dye precursors include oxidation dye precursors of the developer and coupler types. Particularly suitable oxidation dye precursors of the developer type are selected from at least one compound from the group of p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis-(4-aminophenyl)-1,3-diamino-propane-2-ol, bis-(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo[1,2-a]pyrazol-1-one and the physiologically tolerated salts thereof. Most preferred developer components are selected from p-toluylendiamine, 2-(2-hydroxyethyl)-p-phenylendiamine, N,N-bis-(2-hydroxyethyl)-p-phenylendiamine, 2-methoxymethyl-p-phenylendiamine and/or 4,5-diamino-1-(2-hydroxyethyl)-pyrazol and the physiologically tolerated salts and mixtures thereof.

Particularly suitable oxidation dye precursors of the coupler type are selected from the group of 3-aminophenol, 5-amino-2-methylphenol, 3-amino-2-chlor-6-methylphenol, 2-hydroxy-4-aminophenoxyethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxy ethyl amino)benzol (2-amino-4-[(2-hydroxyethyl)amino]-anisol), 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof. Most preferred coupler components are selected from 3-aminophenol, 5-amino-2-methylphenol, 3-amino-2-chlor-6-methylphenol, 2-hydroxy-4-aminophenoxyethanol, 2-(2, 4-diaminophenoxy)ethanol, 1-methoxy-2-amino-4-(2-hydroxyethylamino)benzol (2-Amino-4-[(2-hydroxyethyl)amino]-anisol), resorcin, 2-methylresorcin, 4-chlorresorcin, 2-amino-3-hydroxypyridin, as well as the physiologically compatible salts and mixtures thereof.

In a preferred embodiment, the coloring agents as contemplated herein contain one or more oxidation dye precursors in a total quantity from about 0.001 to about 5.0 wt. %, preferably from about 0.01 to about 4.0 wt. %, more preferably from about 0.2 to about 3.5 wt. %, more preferably from about 0.3 to about 2.5 wt. % and very particularly preferably from about 0.7 to about 1.8 wt. %, relative to the weight of the dye as contemplated herein and/or the weight of the composition used as contemplated herein (M1).

In a preferred embodiment, the coloring agents as contemplated herein contain one or more oxidation dye precursors, selected from at least one developer component and optionally at least one coupler component, in a total quantity from about 0.001 to about 5.0 wt. %, preferably from about 0.01 to about 4.0 wt. %, more preferably from about 0.2 to about 3.5 wt. %, more preferably from about 0.3 to about 2.5 wt. % and very particularly preferably from about 0.7 to about 1.8 wt. %, relative to the weight of the dye as contemplated herein and/or the weight of the composition used as contemplated herein (M1).

In a more preferred embodiment of the present disclosure, the agent as contemplated herein contains at least one partially-oxidizing dye. In oxidative hair dyes, partially-oxidizing dyes often serve to tint unwanted red undertones, which can be produced by the melanin decomposition products, or to tint certain blond tones.

In order to obtain a balanced and subtle tint formation, the present disclosure may specify that the cosmetic agents with ODP additionally contain at least one partially-oxidizing dye.

Partially-oxidizing dyes are dyes that coat the substrate itself and do not require an oxidative process to create the color. Partially-oxidizing dyes are usually nitro-phenylendiamines, nitroaminophenols, azo dyes, anthraquinones or indophenols.

Partially-oxidizing dyes can be sub-divided into anionic, cationic and non-ionic partially-oxidizing dyes.

Preferred anionic partially-oxidizing dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue.

Preferred cationic partially-oxidizing dyes are cationic triphenylmethane dyes, such as Basic Blue 7, Basic Blue 26, Basic Violet 2 and Basic Violet 14, as well as aromatic systems, which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chlor-2- nitrobenzol, 4-amino-3-nitrophenol, 1-(2'-Ureidoethyl) amino-4-nitrobenzol, 2-[(4-amino-2-nitrophenyl)amino] benzoic acid, 6-nitro-1,2,3,4-tetrahydrochinoxalin, 2-hydroxy-1,4-naphthochinon, picramic acid and the salts thereof, 2-amino-6-chloro-4-nitrophenol, 4-ethylamino-3-nitrobenzoic acid and 2-chlor-6-ethylamino-4-nitrophenol.

Moreover, partially-oxidizing dyes that occur in nature, such as Henna red, Henna neutral, Henna black, chamomile blossoms sandalwood, black tea, walnut, Cascara bark, sage, logwood, madder root, catechu, ceder and alkanna root, can also be used.

The cosmetic agent according preferably contains at least one partially-oxidizing agent in a total quantity of from about 0.001 to about 10 wt. %, preferably from about 0.01 to about 8 wt. %, more preferably from about 0.1 to about 5 wt. %, most preferably from about 0.5 to about 2 wt. %, relative to the total weight of the cosmetic agent and/or of the composition used as contemplated herein (M1).

Therefore, a further subject of the present disclosure is a kit-of-parts, comprising—packaged separately from one another:
a) at least one container (C1), containing an agent for oxidative hair dyeing containing the following, in each case relative to its weight:
  from about 60-about 83 wt. % water,
  at least one oxidation dye precursor,
  at least one alkalizing agent,
  at least one crosslinked copolymer composed of acrylic acid and non-ethoxylated esters of acrylic acid with linear C10-C30 monoalcohols as monomers, wherein the crosslinked copolymer is present in a total quantity of from about 0.08 to about 0.8 wt. %,
  at least one linear, saturated 1-alkanol with a hydroxy group and from about 8 to about 22 carbon atoms in a total amount of from about 8-about 15 wt. %, preferably from about 8.5-about 14 wt. %, particularly preferably from about 9-about 13 wt. %,
  at least one saturated or unsaturated alkane carboxylic acid with from about 14 to about 22 carbon atoms or a salt thereof in a total amount of from about 0.1-about 2%, preferably from about 0.2-about 1.5% wt. %, more preferred from about 0.3 about-0.8% wt. %,
  in a total quantity of from about 1-about 5% wt. %, preferably from about 1.5-about 4 wt. %, particularly preferred from about 2-about 3 wt. %, at least one glycerol fatty acid from Formula (I)

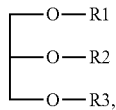

(I)

where
R1, R2 and R3 each independently of one another denote a hydrogen atom or a grouping of Formula (II),

(II)

where
R4 denotes an unbranched or branched, saturated or unsaturated $C_{11}$-$C_{27}$ alkyl group, providing that at least one and a maximum of two of the radicals, selected from R1, R2, and R3, denotes a grouping of Formula (II);
  In addition to the aforementioned substances, at least one other surfactant, selected from anionic, zwitterionic, amphoteric and non-ionic surfactants and mixtures thereof, in a total quantity of from about 1-about 6 wt. %, preferably from about 1.4-about 5 wt. %, and more preferred 2-4.5 wt. %, and
  at least one of branched alkanol with a hydroxy group and from about 10 to about 50 carbon atoms, preferably in a total quantity of from about 0.5-about 5 wt. %, preferably from about 1-about 4% by weight or more preferably from about 1.5-about 3 wt. %.
which contains no oxidants, and
b) at least one container (C2), containing an oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, very particularly preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2).

A further subject matter of the present disclosure is a method for oxidative hair dyeing comprising the following method steps:
i) Providing a cosmetic agent (M1) for the oxidative hair dyeing of keratinic fibers, containing
  from about 60-about 83 wt. % water,
  at least one oxidation dye precursor,
  at least one alkalizing agent,
  at least one crosslinked copolymer composed of acrylic acid and non-ethoxylated esters of acrylic acid with linear C10-C30 monoalcohols as monomers, wherein the crosslinked copolymer is present in a total quantity of from about 0.08 to about 0.8 wt. %,
  at least one linear, saturated 1-alkanol with a hydroxy group and from about 8 to about 22 carbon atoms in a total amount of from about 8-about 15 wt. %, preferably from about 8.5-about 14 wt. %, particularly preferably from about 9-about 13 wt. %,
  at least one saturated or unsaturated alkane carboxylic acid with from about 14 to about 22 carbon atoms or a salt thereof in a total amount of from about 0.1-about 2%, preferably from about 0.2-about 1.5% wt. %, more preferred from about 0.3-about 0.8% wt. %,
  in a total quantity of from about 1-about 5% wt. %, preferably from about 1.5-about 4 wt. %, particularly preferred from about 2-about 3 wt. %, at least one glycerol fatty acid from Formula (I)

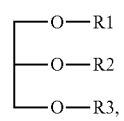

(I)

where
R1, R2 and R3 each independently of one another denote a hydrogen atom or a grouping in Formula (II),

where
- R4 denotes an unbranched or branched, saturated or unsaturated C11-C27 alkyl group,
- providing that at least one and a maximum of two of the radicals, selected from R1, R2, and R3, denotes a grouping of Formula (II);
- In addition to the aforementioned substances, at least one other surfactant, selected from anionic, zwitterionic, amphoteric and non-ionic surfactants and mixtures thereof, in a total quantity of from about 1-about 6 wt. %, preferably from about 1.4-about 5 wt. %, and more preferred from about 2-about 4.5 wt. %, and
- at least one of branched alkanol with a hydroxy group and from about 10 to about 50 carbon atoms, preferably in a total quantity of from about 0.5-about 5 wt. %, preferably from about 1-about 4% by weight or more preferably from about 1.5-about 3 wt. %.

which contains no oxidants, and ii) Providing an oxidant preparation (M2), containing from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, very particularly preferably from about 5 to about 18 wt. % and exceptionally preferred from about 6 to about 12 wt. %, and a pH value in the range from about 2.0 to about 6.5, preferably from about 2.5-about 5.5, most preferably from about 2.8 to about 5.0, having, in each case measured at 20° C., wherein preferably at least one surfactant, selected from anionic surfactants and non-ionic surfactants, as well as mixtures thereof, in a total quantity from about 0.05 about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) as well as mixtures thereof, in a total quantity from about 1-about 5 wt. %, preferably from about 1.5-about 4 wt. %, wherein optionally at least one oil in a total quantity of from about 0.2-about 50 wt. %, preferably from about 2-about 40 wt. %, more preferably from about 8-about 30 wt. %, most preferably from about 15-about 25 wt. %, and/or optionally at least one cationic surfactant, preferably in a total quantity of from about 0.05 about 3 wt. %, more preferably from about 0.1-about 1.5 wt. %, most preferably from about 0.3-about 0.9 wt. %, is contained, wherein all quantity data are relative to the weight of the oxidant preparation (M2), iii) Mixing the cosmetic agent (M1) with the oxidant preparation (M2), preferably in a weight ratio (M1):(M2) in the range from about 1:0.8 to about 1:2.5, preferably from about 1:1 to about 1:2, immediately afterwards iv) Applying the mixture obtained in Step iii) onto the hair and leaving said mixture for a period of from about 1 to about 60 minutes, preferably from about 20 to about 45 minutes at room temperature and/or at from about 30-about 60° C., v) Rinsing the hair with water and/or a cleansing composition, and vi) where necessary, applying a post-treatment agent onto the hair and, where necessary, rinsing out, then drying.

For oxidative hair dyeing, immediately before the application on the hair, the one or more oxidation dye precursors and, where applicable, one or more partially-oxidizing dyes, are usually mixed with a hydrous oxidant-containing composition (M2) to produce the ready-to-use coloring agent and then applied to the hair. In most cases, the agent as contemplated herein (M1) and the oxidant-containing composition (M2) are matched with one another such that, at a mixing ratio of about 1 to 1, relative to the parts by weight, the ready-to-use application mixture has an initial concentration of hydrogen peroxide of from about 0.5-about 12 wt. %, preferably from about 2-about 10 wt. %, more preferably from about 3-about 6 wt. % of hydrogen peroxide (calculated as 100% $H_2O_2$), in each case relative to the weight of the application mixture. However, it is equally possible for the agent as contemplated herein (M1) and the oxidant-containing composition (M2) to be matched to one another such that the concentrations required in the ready-to-use oxidant dye (application mixture) is achieved through mixture ratios other than 1:1, for example through a weight-based mixture ratio of about 1:2 or about 1:3 or even about 2:3.

Weight-based mixture ratios preferred as contemplated herein (M1):(M2) are within the range from about 1:0.8 to about 1:2.5, more preferably within the range of from about 1:1 to about 1:2.

As contemplated herein, the expression "room temperature" describes the temperature inside the room in which a person would usually use a hair coloring agent, i.e. usually a bathroom or a hairdressing salon, in which a temperature within the range of from about 10-about 29° C. prevails.

The leaving of the hair dyeing application mixture in method step iv) in the hair dyeing method as contemplated herein or preferred as contemplated herein can also occur at a minimum of about 30° C., preferably at from about 30-about 60° C., more preferably at from about 32-about 50° C., if the hair is heated by employing a heating hood or a heat radiator, for example.

The oxidant preparation (M2) used in the dye kit as contemplated herein and preferred as contemplated herein, as well as in the dyeing method as contemplated herein and preferred as contemplated herein contains, in each case relative to the weight thereof, from about 40-about 96 wt. %, preferably from about 70-about 93 wt. %, most preferably from about 80-about 90 wt. % of water.

The oxidant preparation (M2) used in the dye kit as contemplated herein and preferred as contemplated herein, as well as in the dyeing method as contemplated herein and preferred as contemplated herein contains, in each case relative to the weight thereof, from about 0.5 to about 23 wt. %, preferably from about 2.5 to about 21 wt. %, more preferably from about 4 to about 20 wt. %, very particularly preferably from about 5 to about 18 wt. and most preferably from about 6 to about 12 wt. % of hydrogen peroxide.

To stabilize the hydrogen peroxide, the oxidant preparation (M2) has a pH value in the range from about 2.0 to about 6.5, preferably from about 2.5-about 5.5, most preferably from about 2.8 to about 5.0, in each case measured at 20° C.

The preferred dye kit as contemplated herein and preferred hair dyeing method as contemplated herein are each exemplified in that the oxidation preparation (M2) contains at least one surfactant, selected from anionic surfactants and nonionic surfactants, as well as mixtures thereof, in a total quantity of from about 0.05-about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5 about 4 wt. %, each relative to the weight of the oxidant preparation (M2).

The anionic surfactants and nonionic surfactants in the oxidant preparations (M2) as contemplated herein are selected from the same surfactants from which the anionic surfactants and nonionic surfactants contained in the agent(s) as contemplated herein (M1) are selected.

According to the present application, the above linear, saturated 1-alkanols with one hydroxyl group, alkane carboxylic acids with from about 14 to about 22 carbon atoms and glycerol fatty acid esters of Formula (I) in relation to the oxidant preparations (M2) are not counted as surfactants.

In a more preferred embodiment of the present disclosure, the oxidant preparation (M2) used as contemplated herein contains at least one oil in a total quantity of from about 0.2-about 50 wt. %, preferably from about 2-about 40 wt. %, more preferably from about 8-about 30 wt. %, most preferably from about 15-about 25 wt. %, in each case relative to the weight of the oxidant preparation (M2).

The at least one oil contained in the oxidant preparation (M2) in a total quantity of from about 0.2-about 50 wt. %, preferably from about 2-about 40 wt. %, more preferably from about 8-about 30 wt. %, most preferably from about 15-about 25 wt. % relative to the weight of the preparation (M2), is preferably selected from natural and synthetic hydrocarbons, particularly preferred from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from about 2-about 30 carbon atoms with linear or branched saturated or unsaturated fatty acids having from about 2-about 30 carbon atoms, which can be hydroxylated; the adducts of from 1 to about 5 propylenoxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkandiols or $C_{3-22}$ alkantriols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. In this context, oils particularly preferred as contemplated herein are selected from paraffin oils and the esters of linear or branched saturated or unsaturated fat alcohols having from about 2-about 30 carbon atoms with linear or branched fatty acids having from about 2-about 30 carbon atoms, which can be hydroxylated, as well as mixtures thereof, most preferred oils are selected from paraffin oil, isopropylpalmitate and isopropylmyristate, as well as mixtures thereof.

A further preferred kit of parts and a further hair coloring method preferred as contemplated herein are each exemplified in that the oxidant preparation (M2) contains at least one oil in a total quantity of from about 0.2-about 50 wt. %, preferably from about 2 about 40 wt. %, particularly preferably from about 8-about 30 wt. %, especially preferred from about 15-about 25 wt. %, in each case relative to the weight of the oxidant preparation (M2), and preferably does not contain any cationic surfactants.

A further kit-of-parts preferred as contemplated herein and a further hair coloring method preferred as contemplated herein are each exemplified in that the oxidant preparation (M2) contains at least one oil in a total quantity of from about 0.2-about 50 wt. %, preferably from about 2-about 40 wt. %, particularly preferably from about 8-about 30 wt. %, extraordinarily preferred from about 15-about 25 wt. %, in each case relative to the weight of the oxidant preparation (M2), but contains no polymer with a polymerization degree of at least 200 and no polymer with a molecular weight of 10,000 Dalton or higher.

A further kit-of-parts preferred as contemplated herein and a further hair coloring method preferred as contemplated herein are each exemplified in that the oxidant preparation (M2) contains at least one oil in a total quantity of from about 0.2-about 50 wt. %, preferably from about 2-about 40 wt. %, particularly preferably from about 8-about 30 wt. %, extraordinarily preferred from about 15-about 25 wt. %, in each case relative to the weight of the oxidant preparation (M2), but contains no polymer with a polymerization degree of at least 200 and no polymer with a molecular weight of 10,000 Dalton or higher.

Cationic Surfactants in the Oxidant Preparation (M2)

The viscosity of the agents as contemplated herein (M1) in the range of from about 17,000-about 40,000 mPas, preferably from about 19,000-about 30,000 mPas, particularly preferably from about 22,000-about 27,000 mPas, measured at 20° C. with a rotation viscosimeter (Haake VT 550) with a rotation frequency of 7.2 s$^{-1}$ with measuring geometry SV II in each case, is outstandingly suitable for the handling of this agent itself (production, dispensing, metering for production of the mixture with the oxidant preparation). The oxidant preparation (M2) usually has a low viscosity in the range of from about 10-about 6000 mPas, preferably from about 200-about 5000 mPas, particularly preferably from about 1000-about 4500 mPas, measured at 20° C. in each case. For application on the hair, however, the application mixture ought to have a substantially higher viscosity so that it remains on the hair for the entire exposure time (in the range of from about 5-about 60 minutes, preferably from about 30-about 45 minutes) without dripping. A distinction is drawn here as to whether the application mixture is produced by shaking the two compositions (M1) and (M2) in an application bottle, from which the application mixture is applied to the hair immediately after mixing by employing an application nozzle in the form of a bottle attachment (bottle application), or whether the application mixture is produced by stirring the two compositions (M1) and (M2) in a bowl, from which the application is mixture is applied to the hair immediately after mixing by employing a brush (brush application). The bottle application is particularly suitable for coloring agents that are sold in retail outlets trade with an application recommendation by the consumer itself. The brush application is particularly suitable for coloring agents that are produced in the hairdressing salon and applied to the consumer's hair by the hairdresser.

It has unexpectedly emerged that an application mixture having a viscosity particularly suitable for brush application is obtained if the agent as contemplated herein or preferred as contemplated herein (M1) is mixed with an oxidant preparation (M2) containing at least one cationic surfactant. During mixing, the interaction between the at least one crosslinked copolymer of acrylic acid and non-ethoxylated esters of acrylic acid with linear C10-C30 monoalcohols and the at least one cationic surfactant leads to the desired increase in viscosity. The pasty consistency of the application mixture thus obtained leads to optimum application properties, more particularly for the brush application. The application mixtures thus achieved, particularly with weight-based mixture ratios (M1):(M2) in the range of from about 1:0.8 to about 1:2.5, preferably have a viscosity in the range of from about 10,000 about 100,000 mPas, preferably from about 12,000-about 80,000 mPas, particularly preferably from about 15,000-about 40,000 mPas, in each case measured at 20° C. with a Brookfield viscometer, at a rotational frequency of 4 rpm with Spindle No. 5.

In a more preferred embodiment of the present disclosure, the oxidant preparation used as contemplated herein (M2) contains at least one cationic surfactant, preferably in a total quantity of from about 0.05-about 3 wt. %, particularly preferably from about 0.1-about 1.5 wt. %, exceptionally preferred from about 0.3-about 0.9 wt. %, in each case relative to the weight of the oxidant preparation (M2).

Cationic surfactants are surfactants, i.e. surfactant compounds, each having one or more positive charges. Cationic surfactants contain exclusively positive charges. Usually, said surfactants are constructed from a hydrophobic part and a hydrophilic head group, wherein the hydrophobic part normally includes a hydrocarbon structure (e.g. including one or two linear or branched alkyl chains), and the positive charge(s) are localized in the hydrophilic head group. Cationic surfactants adsorb at boundary surfaces and aggregate in hydrous solutions above the critical micelle formation concentration to form positively charged micelles.

As contemplated herein, preferred cationic surfactants are of the type of quaternary ammonium compounds, eterquats and alkyl amidoamines. Preferred quaternary ammonium compounds are ammonium halogenides, such as alkyltrimethylammoniumchloride, dialkyldimethylammoniumchloride, trialkylmethylammoniumchloride, as well as the imidazolium compounds known under the INCI trade names of Quaternium-27 and Quaternium-83. Additional preferred quaternary ammonium compounds are tetraalkylammonium salts, particularly known under the INCI designation the quaternium-52, a poly(oxy-1,2-ethanediyl), ((octadecylnitrilo)tri-2,1-ethanediyl)tris(hydroxy) phosphate (1:1)-salt, which has the general structural formula (III), wherein x+y+z=10:

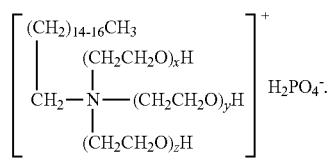
(III)

The long alkyl chains of the aforementioned surfactants preferably have from about 10 to about 22, particularly preferably from about 12 to about 18 carbon atoms. Particularly preferred are behenyl trimethyl ammonium chloride, stearyl trimethyl ammonium chloride and cetyl trimethyl ammonium chloride, wherein stearyl trimethyl ammonium chloride is most preferred. Other suitable cationic surfactants as contemplated herein are quaternary protein hydrolysates. Alkylamidoamines are usually produced through the amidation of natural or synthetic fatty acids and fatty acid molecules with dialkylaminoamines. As contemplated herein, Tegoamid® S 18 (stearamidopropyldimethylamine) is a suitable compound from this substance group. Esterquats are substances containing both at least one ester function and at least quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. Such products are sold under the trade names of Stepantex, Dehyquart and Armocare.

With respect to optimum application properties and optimum dye results, C10-C22 alkyl trimethyl ammonium chloride has proved to be particularly suitable. Particularly preferred oxidant preparations used as contemplated herein (M2) are therefore exemplified in that they contain at least one cationic surfactant in a total quantity from about 0.05-about 3 wt. %, particularly preferably from about 0.1-about 1.5 wt. %, exceptionally preferred from about 0.3-about 0.9 wt. %, in each case relative to the weight of the oxidant preparation (M2), wherein preferably at least one surfactant is contained, selected from C10-C22 alkyl trimethyl ammonium chlorides, most preferably selected from behenyl trimethyl ammonium chloride, stearyl trimethyl ammonium chloride and cetyl trimethyl ammonium chloride, as well as mixtures of said surfactants. Particularly preferred oxidant preparations (M2) used as contemplated herein contain stearyltrimethylammonium chloride in a total amount of from about 0.05-about 3 wt. %, preferably from about 0.1-about 1.5 wt. %, particularly from about 0.3-about 0.9 wt. %, relative to the weight of the oxidant preparation (M2) in each case.

A further kit-of-parts preferred as contemplated herein and a further hair coloring method preferred as contemplated herein are each exemplified in that the oxidant preparation (M2) contains at least one cationic surfactant, preferably in a total quantity of from about 0.05-about 3 wt. %, particularly preferably from about 0.1-about 1.5 wt. %, exceptionally preferred from about 0.3-about 0.9 wt. %, in each case relative to the weight of the oxidant preparation (M2).

A further kit-of-parts and a further hair coloring method preferred as contemplated herein are each exemplified in that the oxidant preparation (M2) contains at least one cationic surfactant, preferably in a total quantity of from about 0.05-about 3 wt. %, particularly preferably from about 0.1-about 1.5 wt. %, exceptionally preferred from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

It has emerged that the thickening aided by the interaction between the copolymer in the agent as contemplated herein and the cationic surfactant in the oxidant preparation (M2) is adequate, and due to the presence of a polymer with a polymerization degree of at least about 200 or a polymer with a molecular weight of about 10,000 Dalton or higher, is unable to further increase and/or even be adversely affected in terms of its application properties.

A more preferred kit-of-parts as contemplated herein and a more preferred hair dyeing method as contemplated herein are each exemplified in that the oxidation preparation (M2) contains at least one surfactant, selected from anionic surfactants and non-ionic surfactants, as well as mixtures thereof, in a total quantity of from about 0.05-about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, each relative to the weight of the oxidant preparation (M2).

A more preferred kit-of-parts as contemplated herein and a more preferred hair dyeing method as contemplated herein are each exemplified in that the oxidation preparation (M2) contains at least one surfactant, selected from anionic surfactants and non-ionic surfactants, as well as mixtures thereof, in a total quantity of from about 0.05-about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, each relative to the weight of the oxidant preparation (M2), although no polymers having a polymerization degree of at least about 200 and no polymer having a molecular weight of about 10,000 Dalton or higher.

It has emerged that the thickening aided by the interaction between the copolymer in the agent as contemplated herein and the aforementioned surfactant/1-alkanol mixture in the oxidant preparation (M2) is adequate, and due to the presence of a polymer with a polymerization degree of at least about 200 or a polymer with a molecular weight of about 10,000 Dalton or higher, is unable to further increase and/or even be adversely affected in terms of its application properties.

A more preferred kit-of-parts as contemplated herein and a more preferred hair dyeing method as contemplated herein are each exemplified in that the oxidation preparation (M2) contains at least one surfactant, selected from anionic surfactants and non-ionic surfactants, as well as mixtures thereof, in a total quantity of from about 0.05-about 2 wt. %, preferably from about 0.3-about 1.5 wt. %, at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, and at least one oil in a total quantity of from about 0.2-about 50 wt. %, preferably from about 2-about 40 wt. %, particularly preferably from about 8-about 30 wt. %, exceptionally preferred from about 15-about 25 wt. %, each relative to the weight of the oxidant preparation (M2).

A more preferred kit-of-parts as contemplated herein and a more preferred hair dyeing method as contemplated herein are each exemplified in that the oxidation preparation (M2) contains at least one surfactant, selected from anionic surfactants and non-ionic surfactants, as well as mixtures thereof, in a total quantity of from about 0.05-about 2 wt. %, preferably from about 0.3-about 1.5 wt. %, at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, and at least one oil in a total quantity of from about 0.2-about 50 wt. %, preferably from about 2-about 40 wt. %, particularly preferably from about 8-about 30 wt. %, most preferably from about 15-about 25 wt. %, each relative to the weight of the oxidant preparation (M2), although no polymers having a polymerization degree of at least about 200 and no polymers having a molecular weight of about 10,000 Dalton or higher.

It has unexpectedly emerged that an application mixture having a viscosity particularly suitable for bottle application is obtained if the agent as contemplated herein or preferred as contemplated herein (M1) is mixed with an oxidant preparation (M2) containing at least one copolymer, selected from cross-linked acrylic acid/acrylic acid-C1-C6-alkyl ester copolymers and cross-linked methacrylic acid/acrylic acid-C1-C6-alkyl ester copolymers, preferably in a total quantity from about 0.1-about 7 wt. %, particularly preferably from about 0.5-about 6 wt. %, most preferably from about 1-about 4.5 wt. %, in each case relative to the weight of the oxidant preparation (M2). The mixing of the agent as contemplated herein or preferred as contemplated herein with such an oxidation preparation (M2) leads to the desired viscosity increase. The medium-viscosity consistency of the application mixture thus obtained leads to optimum application properties, more particularly for the bottle application. The application mixtures thus achieved, particularly with weight-based mixture ratios (M1):(M2) in the range of from about 1:0.8 to about 1:2.5, preferably have a viscosity in the range of from about 10,000-about 100,000 mPas, preferably from about 12,000-about 80,000 mPas, particularly preferably from about 15,000-about 40,000 mPas, in each case measured at 20° C. with a Brookfield viscometer, at a rotational frequency of 4 rpm with Spindle No. 5.

A further kit-of-parts preferred as contemplated herein is exemplified in that the oxidant preparation (M2) contains at least one copolymer, selected from cross-linked acrylic acid/acrylic acid-C1-C6 alkyl ester-copolymers and cross-linked methacrylic acid/acrylic acid-C1-C6-alkyl ester copolymers, preferably in a total quantity of from about 0.1-about 7 wt. %, particularly preferably from about 0.5-about 6 wt. %, exceptionally preferred from about 1-about 4.5 wt. %, in each case relative to the weight of the oxidant preparation (M2), and preferably contains no cationic surfactant.

A further method for oxidative hair dyeing as contemplated herein is exemplified in that the oxidant preparation (M2) contains at least one copolymer, selected from cross-linked acrylic acid/acrylic acid-C1-C6 alkyl ester-copolymers and cross-linked methacrylic acid/acrylic acid-C1-C6-alkyl ester copolymers, preferably in a total quantity of from about 0.1-about 7 wt. %, particularly preferably from about 0.5-about 6 wt. %, exceptionally preferred from about 1-about 4.5 wt. %, in each case relative to the weight of the oxidant preparation (M2), and preferably contains no cationic surfactant.

Preferred cross-linked copolymers of this type are selected from in each case cross-linked—methacrylic acid/methylacrylate-, methacrylic acid/ethyl acrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate copolymers and the mixtures thereof.

A further kit-of-parts preferred as contemplated herein is exemplified in that the oxidant preparation (M2) contains at least one cross-linked copolymer, selected from in each case cross-linked—methacrylic acid/methylacrylate-, methacrylic acid/ethylacrylate-, methacrylic acid/propylacrylate-, methacrylic acid/buty lacrylate-, methacrylic acid/pentylacrylate-, methacrylic acid/hexylacrylate-, acrylic acid/methacrylic acrylate-, acrylic acid/ethyl acrylate-, acrylic acid/propylacrylate-, acrylic acid/butylacrylate, acrylic acid/pentyl acrylate- and acrylic acid/hexylacrylate-copolymers and mixtures thereof, in a total quantity from about 0.1-about 7 wt. %, particularly preferably from about 0.5-about 6 wt. %, exceptionally preferred from about 1-about 4.5 wt. %, in each case relative to the weight of the oxidant preparation (M2), and no cationic surfactant.

A further preferred method for oxidative hair coloring as contemplated herein is exemplified in that the oxidant preparation (M2) contains at least one crosslinked copolymer selected from—crosslinked in each case—methacrylic acid/methacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethyl acrylate-, acrylic acid/propylacrylate-, acrylic acid/butylacrylate-, acrylic acid/pentylacrylate- and acrylic acid/hexylacrylate-copolymers and mixtures thereof, in a total amount of from about 0.1-about 7 wt. %, particularly preferably from about 0.5-about 6 wt. %, particularly from about 1-about 4.5 wt. %, relative to the weight of the oxidant preparation (M2) in each case, and preferably containing no cationic surfactants.

Moreover, the oxidant preparations as contemplated herein and preferred as contemplated herein (M2) can contain stabilizers, more particularly complexing agents, and pH buffer substances.

With respect to the cosmetic agent (M1) in container C1 and the oxidant preparation (M2) in container C2 of the kit as contemplated herein and preferred as contemplated herein, the statements made about the agents as contemplated herein and preferred as contemplated herein apply mutatis mutandis.

With respect to the cosmetic agent (M1) in container C1 and the method for oxidative hair dyeing as contemplated herein and preferred as contemplated herein, the statements made about the agents as contemplated herein and preferred as contemplated herein apply mutatis mutandis.

With respect to oxidant preparation (M2) in container C1 and the method for oxidative hair dyeing as contemplated herein and preferred as contemplated herein, the statements made about the oxidant preparations (M2) of the kits as contemplated herein and preferred as contemplated herein apply mutatis mutandis.

The container wall of container C1 and C2 is preferably made of a polyolefin, such as polypropylene (PP), high density polyethylene (HDPE), medium density polyethylene (MDPE), low density polyethylene (LDPE), linear low density polyethylene (LLDPE). Polyethylene is particularly suitable, in particular high density polyethylene (HDPE). For improved intermixing of (M1) and (M2), it is preferred that the container (C2) containing the oxidizing agent preparation (M2) is designed as a bottle and has a re-closable opening, such as, a snap-action or screw-type closure. This enables easier addition of color-changing agent from container (C1), which is preferably designed as a bottle made of a polyolefin.

The following examples are intended to explain the subject matter of the present disclosure without having any limiting effect.

Examples

TABLE 1

Dye cream for oxidative hair coloring

| Ingredient | V 1 (wt. %) | V 2 (wt. %) | E1 (wt. %) |
|---|---|---|---|
| Sodium cetearyl sulfate | 0.74 | 0.74 | 0.50 |
| Sodium laureth(2)sulphate | 1.33 | 1.33 | 1.00 |

TABLE 1-continued

Dye cream for oxidative hair coloring

| Ingredient | V 1 (wt. %) | V 2 (wt. %) | E1 (wt. %) |
|---|---|---|---|
| Potassium hydroxide | 0.08 | 0.08 | 0.06 |
| Oleic acid | 0.40 | 0.40 | 0.30 |
| Cetearyl alcohol | 12.60 | 12.60 | 9.50 |
| Ceteareth-20 | 3.20 | 3.20 | 2.40 |
| 2-octyldodecanol | 2.20 | 2.20 | 1.60 |
| Glycerol | 1.00 | 1.00 | 1.00 |
| glyceryl stearate (1:1 mixture of glyceryl monostearate and glyceryl distearate) | 4.00 | 4.00 | 3.00 |
| Potassium stearate | 0.40 | 0.40 | 0.30 |
| Titanium dioxide | 0.50 | 0.50 | 0.50 |
| Sodium sulfate | 0.10 | 0.10 | 0.10 |
| Monoethanolamine (2-aminoethan-1-ol) | 0.20 | 0.20 | 0.20 |
| Ammonium hydroxide | 3.20 | 3.20 | 3.20 |
| Acrylates/C10-30 Alkyl Acrylate Crosspolymer | — | 0.03 | 0.15 |
| Polyquaternium-39 | 0.20 | 0.20 | 0.20 |
| Tetrasodium EDTA | 0.30 | 0.30 | 0.30 |
| Ascorbic acid | 0.05 | 0.05 | 0.05 |
| Toluen-2,5-diaminsulphate | 0.41 | 0.41 | 0.41 |
| Resorcin | 0.10 | 0.10 | 0.10 |
| m-aminophenol | 0.01 | 0.01 | 0.01 |
| 4-chlororesorcin | 0.06 | 0.06 | 0.06 |
| Naphtalene-2,7-diol | 0.01 | 0.01 | 0.01 |
| 2-Methyl resorcin | 0.04 | 0.04 | 0.04 |
| Carbomer | 0.17 | — | — |
| Water | 68.70 | 68.84 | 74.11 |
| Viscosity [mPas]* | 19,300 | 20,200 | 25,000 |

*Viscosity, measured at 20° C. with a rotation viscosimeter (Haake VT 550) with a rotation frequency of 7.2 s$^{-1}$ with measurement geometry SV E1 is an agent as contemplated herein (M1); V1 and V2 are comparison compositions. The comparison in Table 1 shows that acrylates/C10-30 alkyl acrylate crosspolymers, in a quantity of at least 0.08 wt. % has stronger thickening effect than 0.17 wt. % carbomers and a higher proportion of—in particular fixed-fats (cetearyl alcohol, glyceryl stearate etc.).

TABLE 2

Developers containing oxidant for the color cream from Table 1

| Ingredient | Test sample (wt. %) |
|---|---|
| Sodium benzoate | 0.04 |
| Dipicolinic acid (2,6-dicarboxypyridin) | 0.10 |
| Di-sodium pyrophosphate | 0.10 |
| Potassium hydroxide | 0.10 |
| 1,2-Propanediol | 0.50 |
| Etidronic acid | 0.15 |
| Paraffin oil | 2.00 |
| Cetearyl alcohol | 3.40 |
| Ceteareth-20 | 1.00 |
| Hydrogen peroxide | 6.00 |
| Water | ad 100.00 |

Viscosity: 3500 mPas, measured at 20° C. with a rotation viscosimeter (Haake VT 550) with a rotation frequency of 4 rpm with measurement geometry MV II

TABLE 3

Developers containing oxidant for the color cream from Table 1

| Ingredient | Test sample (wt. %) |
|---|---|
| Sodium benzoate | 0.04 |
| Dipicolinic acid (2,6-dicarboxypyridin) | 0.10 |

TABLE 3-continued

Developers containing oxidant for the color cream from Table 1

| Ingredient | Test sample (wt. %) |
|---|---|
| Di-sodium pyrophosphate | 0.10 |
| Potassium hydroxide | 0.10 |
| 1,2-Propanediol | 1.00 |
| Etidronic acid | 0.15 |
| Paraffin oil | 0.30 |
| Stearyl trimethyl ammonium chloride | 0.30 |
| Cetearyl alcohol | 3.40 |
| Ceteareth-20 | 1.00 |
| Hydrogen peroxide | 6.00 |
| Water | ad 100.00 |

Viscosity: 4500 mPas, measured at 20° C. with a rotation viscosimeter (Haake VT 550) with a rotation frequency of 4 rpm with measurement geometry MV II

TABLE 4

Developers containing oxidant for the color cream from Table 1

| Ingredient | Test sample (wt. %) |
|---|---|
| Sodium hydroxide | 0.40 |
| Dipicolinic acid (2,6-dicarboxypyridin) | 0.10 |
| Di-sodium pyrophosphate | 0.03 |
| Etidronic acid | 0.15 |
| Mixture of cross-linked (meth)acrylic acid/ acrylic acid-C1-C6-alkyl ester copolymers (ex Aculyn 33A) | 4.20 (active) |
| Sodium laureth(2)sulphate | 0.50 |
| Hydrogen peroxide | 6.00 |
| Water | ad 100.00 |

* Aculyn 33A: hydrous dispersion of Acrylates Copolymer (mixture of cross-linked (meth)acrylic acid/acrylic acid-C1-C6-alkyl ester copolymers); 28 wt. % polymer content (active substance)

Viscosity: * Viscosity: measured at 20° C. by employing a Brookfield rotational viscometer at a rotational frequency of 20 rpm with Spindle 2

TABLE 5

Developers containing oxidant for the color cream from Table 1

| Ingredient | Test sample (wt. %) |
|---|---|
| Sodium benzoate | 0.04 |
| Dipicolinic acid (2,6-dicarboxypyridin) | 0.10 |
| Di-sodium pyrophosphate | 0.10 |
| Potassium hydroxide | 0.12 |
| Etidronic acid | 0.15 |
| Paraffin oil | 20.00 |
| Sodium cetearyl sulfate | 0.36 |
| Cetearyl alcohol | 3.50 |
| PEG-40 Castor Oil | 0.70 |
| Hydrogen peroxide | 6.00 |
| Water | ad 100.00 |

Viscosity: 7,500 mPas, measured at 20° C. with a rotation viscosimeter (Haake VT 550) with a rotation frequency of 4 rpm with measurement geometry MV II

TABLE 6

Developers containing oxidant for the color cream from Table 1

| Ingredient | Test sample (wt. %) |
|---|---|
| Sodium benzoate | 0.04 |
| Di-sodium pyrophosphate | 0.10 |
| Potassium hydroxide | 0.12 |
| Etidronic acid | 0.15 |

TABLE 6-continued

Developers containing oxidant for the color cream from Table 1

| Ingredient | Test sample (wt. %) |
|---|---|
| Sodium cetearyl sulfate | 0.20 |
| Cetearyl alcohol | 1.70 |
| PEG-40 Castor Oil | 0.40 |
| Hydrogen peroxide | 6.00 |
| Water | ad 100.00 |

Viscosity: 2500 mPas, measured at 20° C. with a rotation viscosimeter (Haake VT 550) with a rotation frequency of 4 rpm with measurement geometry MV II Production of the Application Mixtures and Coloration on Hair Dye gel and developer according to Table 7 were mixed with one another in a homogeneous manner. The application mixtures thus obtained were applied, immediately after production, to human hair (natural white hair, Kerling) (liquor ratio 4 gram application mixture per gram of hair and left on the hair for 30 minutes at room temperature (22° C.). The strands were then rinsed out and towel-dried.

TABLE 7

Production of the application mixtures for coloration on hair

| Alkaline dye cream (M1) | Developer (M2) | Weight ratio (M1):(M2) | Viscosity of the application mixture [mPas]** |
|---|---|---|---|
| according to Table 1 | according to Table 2 | 1:2 | 36,900 |
| according to Table 1 | according to Table 2 | 1:1 | 42,900 |

**measured at 20° C. by employing a Brookfield rotational viscometer at a rotational frequency of 4 rpm with Spindle 5.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. Agent for oxidative hair dyeing comprising, relative to the weight of the agent,
   from about 60 to about 83 wt. % water,
   at least one oxidation dye precursor,
   at least one alkalizing agent,
   at least one cross-linked copolymer, constructed from acrylic acid and non-ethoxylated esters of acrylic acid with linear C10-C30 mono-alcohols as monomers, wherein the cross-linked copolymer is included in a total quantity of from about 0.08 to about 0.8 wt. %, relative to the weight of the agent,
   at least one linear, saturated 1-alkanol with a hydroxy group and from about 8 to about 22 carbon atoms in a total amount of from about 8 to about 15 wt. %, at least one saturated or unsaturated alkane carboxylic acid with from about 14 to about 22 carbon atoms or a salt thereof in a total amount of from about 0.1 to about 2 wt. %, in a total quantity of from about 1 to about 5% wt. %, at least one glycerol fatty acid from Formula (I)

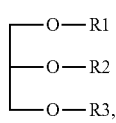
(I)

where
R1, R2 and R3 each independently of one another denote a hydrogen atom or a grouping in Formula (II),

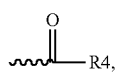
(II)

where
R4 denotes an unbranched or branched, saturated or unsaturated $C_{11}$-$C_{27}$ alkyl group, providing that at least one and a maximum of two of the radicals, selected from R1, R2, and R3, denotes a grouping of Formula (II);
in addition to the aforementioned substances, at least one other surfactant, selected from anionic, zwitterionic, amphoteric and non-ionic surfactants and mixtures thereof, in a total quantity of from about 1 to about 6 wt. %, and which do not contain any oxidants, and
at least one of branched alkanol with a hydroxy group and from about 10 to about 50 carbon atoms,
wherein the agent has a viscosity of from about 22,000 to about 27,000 mPas when measured at 20° C. using a rotational viscometer at a rotational frequency of 7.2 $s^{-1}$ with measurement geometry SV II.

2. Agent according to claim 1, wherein the alkalizing agent is selected from the group comprising ammonium hydroxide, basic amino acids, alkalihydroxides, alkanolamines, alkali metal metasilicates, alkali phosphates and alkali hydrogen phosphates, or the mixtures thereof.

3. Agent according to claim 1, wherein at least one anionic or zwitterionic surfactant is present and is selected from $C_8$-$C_{20}$ alkyl sulphates, $C_8$-$C_{20}$-alkyl ether sulphates and $C_8$-$C_{20}$ ether carboxylic acids, each with from about 8 to about 20 C-atoms in the alkyl group and from about 0 to about 12 ethylene oxide groups in the molecule, cocoacylaminopropyl-dimethyl ammonium glycinate, or from mixtures of said surfactants.

4. Agent according to claim 1, wherein the at least one crosslinked copolymer is constructed from about 80 to about 99 wt. % of acrylic acid and from about 0.9 to about 19.9% of non-ethoxylated esters of acrylic acid with linear C10-C30-monoalcohols, relative to the weight of the at least one crosslinked copolymer.

5. Agent according to claim 1, having a pH value in the range of from about 8 to about 12, measured at 20° C.

6. Agent according to claim 1, wherein the at least one branched alcohol with a hydroxy group and from about 10 to about 50 carbon atoms is selected from 2-hexyldecanol, 2-ocyltdodecanol, 2-ethylhexylalcohol and isostearylalcohol, or mixtures thereof.

7. Kit-of-parts comprising—packaged separately from one another—
a) at least one container (C1), comprising an agent for oxidative hair dyeing according claim 1, and
b) at least one container (C2), comprising an oxidant preparation (M2), which comprises from about 40 to about 96 wt. % of water, hydrogen peroxide in a total quantity of from about 0.5 to about 23 wt. %, and which has a pH value in the range from about 2.0 to about 6.5, measured at 20° C., wherein each of the wt. % values are relative to the weight of the oxidant preparation (M2).

8. The kit-of-parts according to claim 7 is wherein the oxidation preparation (M2) comprises at least one surfactant, selected from anionic surfactants and nonionic surfactants, or mixtures thereof, in a total quantity of from about 0.05 to about 2 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), or mixtures thereof, in a total quantity of from about 1 to about 5 wt. %, relative to the weight of the oxidant preparation (M2).

9. The kit-of-parts according to claim 7 wherein the oxidant preparation (M2) comprises at least one oil in a total amount of from about 0.2 to about 50 wt. %, relative to the weight of the oxidant preparation (M2).

10. Kit-of-parts according to claim 7 wherein the oxidant preparation (M2) comprises at least one cationic surfactant.

11. Kit-of-parts according to claim 7 wherein the oxidant preparation (M2) comprises no polymer with a polymerization degree of at least about 200 and no polymer with a molecular weight of about 10000 Dalton or higher.

12. Kit-of-Parts according to claim 7, wherein the oxidant preparation (M2) comprises no cationic surfactants.

13. Method for oxidative hair dyeing, comprising the following method steps:
i) Providing a cosmetic agent (M1) for oxidative hair dyeing according to claim 1,
ii) Providing an oxidant preparation (M2), comprising from about 40 to about 96 wt. % of water, hydrogen peroxide in a total quantity of from about 0.5 to about 23 wt. %, and a pH value in the range from about 2.0 to about 6.5, measured at 20° C., at least one surfactant, selected from anionic surfactants and non-ionic surfactants, or mixtures thereof, in a total quantity from about 0.05 to about 2 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) or mixtures thereof, in a total quantity from about 1 to about 5 wt. %, wherein optionally at least one oil in a total quantity of from about 0.2 to about 50 wt. %, and/or optionally at least one cationic surfactant, is included, wherein all quantity data are relative to the weight of the oxidant preparation (M2),
iii) Mixing the cosmetic agent (M1) with the oxidant preparation (M2), immediately afterwards
iv) Applying the mixture obtained in Step iii) onto the hair and leaving said mixture for a period of from about 1 to about 60 minutes, at room temperature or from about 30 to about 60° C.,
v) Rinsing the hair with water and/or a cleansing composition, and
vi) where necessary, applying a post-treatment agent onto the hair and, where necessary, rinsing out, then drying.

14. Method for oxidative hair coloring according to claim 13, wherein the oxidant preparation (M2) comprises no polymer with a polymerization degree of at least about 200 and no polymer with a molecular weight of about 10000 Dalton or higher.

15. Agent according to claim 1, wherein the at least one of branched alkanol with a hydroxy group and from about 10 to about 50 carbon atoms is included in a total quantity of from about 0.5 to about 5 wt. %, relative to the total weight of the agent.

16. Agent according to claim 3, wherein the at least one anionic or zwitterionic surfactant is included in a total quantity of from about 0.3 to about 1.5 wt. %, relative to the weight of the agent.

17. Agent according to claim 1, having a pH value in the range of from 9.5 to 10.5, measured at 20° C.

18. Agent according to claim 1, wherein the at least one branched alcohol with a hydroxy group and from about 10 to about 50 carbon atoms is 2-ocyltdodecanol.

19. Agent according to claim 1, wherein:
the at least one cross-linked copolymer is included in a total quantity of from about 0.15 to about 0.3 wt. %
the at least one linear, saturated 1-alkanol with a hydroxy group and from about 8 to about 22 carbon atoms is included in a total amount of from about 9 to about 13 wt. %,
the at least one saturated or unsaturated alkane carboxylic acid with from about 14 to about 22 carbon atoms or a salt thereof is included in a total amount of from about 0.3 to about 0.8% wt. %,
the at least one glycerol fatty acid of Formula (I) is included in a total quantity of from about 2 to about 3 wt. %,
the at least one other surfactant, selected from anionic, zwitterionic, amphoteric and non-ionic surfactants and mixtures thereof, is included in a total quantity of from about 2 to about 4.5 wt. %, and
the at least one of branched alkanol with a hydroxy group and from about 10 to about 50 carbon atoms is included in a total quantity of from about 1.5 to about 3 wt. %,
the agent has a pH value in the range of from about 8 to about 12, measured at 20° C.,
wherein all amounts are relative to weight of the agent.

20. Agent for oxidative hair dyeing comprising, relative to the weight of the agent,
from about 60 to about 83 wt. % water,
at least one oxidation dye precursor,
at least one alkalizing agent,
at least one cross-linked copolymer, constructed from acrylic acid and non-ethoxylated esters of acrylic acid with linear C10-C30 mono-alcohols as monomers, wherein the cross-linked copolymer is included in a total quantity of from about 0.08 to about 0.15 wt. %,
cetearyl alcohol in a total quantity of from about 9 to about 13 wt. %,
oleic acid in a total quantity of from about 0.3 to about 0.8 wt. %,
a mixture of glyceryl monostearate and glyceryl distearate in a total quantity of from about 2 to about 3 wt. %,
in addition to the aforementioned substances, at least one other surfactant selected from anionic, zwitterionic, amphoteric, and non-ionic surfactants and mixtures thereof in a total quantity of from about 0.3 to about 1.5 wt. % and which do not contain any oxidants, and
2-ocyltdodecanol in a total quantity of from about 0.5 to about 5 wt. %,
wherein the agent has a viscosity of from about 22,000 to about 27,000 mPas when measured at 20° C. using a rotational viscometer at a rotational frequency of 7.2 $s^{-1}$ with measurement geometry SV II.

* * * * *